(12) United States Patent
Stehning et al.

(10) Patent No.: US 10,557,904 B2
(45) Date of Patent: Feb. 11, 2020

(54) DETECTION OF BONE TISSUE USING MAGNETIC RESONANCE IMAGING

(71) Applicant: KONINKLIJKE PHILIPS N.V., Eindhoven (NL)

(72) Inventors: Christian Stehning, Eindhoven (NL); Nicole Schadewaldt, Eindhoven (NL); Michael Gunter Helle, Eindhoven (NL); Steffen Renisch, Eindhoven (NL); Heinrich Schulz, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1114 days.

(21) Appl. No.: 14/781,596

(22) PCT Filed: Mar. 27, 2014

(86) PCT No.: PCT/EP2014/056145
§ 371 (c)(1),
(2) Date: Oct. 1, 2015

(87) PCT Pub. No.: WO2014/161766
PCT Pub. Date: Oct. 9, 2014

(65) Prior Publication Data
US 2016/0054416 A1    Feb. 25, 2016

(30) Foreign Application Priority Data
Apr. 2, 2013    (EP) .......................... 1316904

(51) Int. Cl.
*G06K 9/00*    (2006.01)
*G06T 7/00*    (2017.01)
(Continued)

(52) U.S. Cl.
CPC .......... *G01R 33/5602* (2013.01); *A61B 6/037* (2013.01); *A61N 5/1039* (2013.01);
(Continued)

(58) Field of Classification Search
CPC ... G06T 2207/1008; G06T 2207/20076; G06T 2207/20128; G06T 7/11; G06T 7/143; G06T 7/12; A61B 5/055
See application file for complete search history.

(56) References Cited

U.S. PATENT DOCUMENTS

2007/0160278 A1\* 7/2007 Fairbanks ................. G06T 5/20
382/128
2010/0021034 A1    1/2010 Lenglet et al.
(Continued)

FOREIGN PATENT DOCUMENTS

| WO | 2012120422 A1 | 9/2012 |
| WO | 2013001399 A2 | 1/2013 |

OTHER PUBLICATIONS

M. Hoffmann et al, "MRI-Based Attenuation Correction for Whole Body PET/MRI Quantitative Evaluation . . . " The Journal of Nuclear Medicine, vol. 52, No. 9, Sep. 1, 2011.
(Continued)

*Primary Examiner* — Elmer M Chao
(74) *Attorney, Agent, or Firm* — Sherry Austin

(57) ABSTRACT

A medical apparatus (300, 400, 500) includes a magnetic resonance imaging system (302) for acquiring magnetic resonance data (342) from an imaging zone (308); a processor (330) for controlling the medical apparatus; a memory (336) storing machine executable instructions (350, 352, 354, 356). Execution of the instructions causes the processor to: acquire (100, 200) the magnetic resonance data using a pulse sequence (340) which specifies an echo time greater than 400 µs; reconstruct (102, 202) a magnetic
(Continued)

resonance image using the magnetic resonance data; generate (104, 204) a thresholded image (346) by thresholding the magnetic resonance image to emphasize bone structures and suppressing tissue structures in the magnetic resonance image; and generate (106, 206) a bone-enhanced image by applying a background removal algorithm to the thresholded image.

11 Claims, 11 Drawing Sheets

(51) Int. Cl.
*G01R 33/56* (2006.01)
*G01R 33/48* (2006.01)
*A61B 6/03* (2006.01)
*A61N 5/10* (2006.01)
*G01R 33/36* (2006.01)
*G01R 33/385* (2006.01)
*G06K 9/52* (2006.01)
*G06K 9/62* (2006.01)
*G06T 11/00* (2006.01)

(52) U.S. Cl.
CPC ........... *G01R 33/36* (2013.01); *G01R 33/385* (2013.01); *G01R 33/4808* (2013.01); *G01R 33/4828* (2013.01); *G01R 33/5608* (2013.01); *G06K 9/52* (2013.01); *G06K 9/6267* (2013.01); *G06T 7/0012* (2013.01); *G06T 11/003* (2013.01); *G06T 2200/04* (2013.01); *G06T 2207/10088* (2013.01); *G06T 2207/30008* (2013.01)

(56) References Cited

U.S. PATENT DOCUMENTS

| | | | |
|---|---|---|---|
| 2010/0204563 A1 | 8/2010 | Stodilkla et al. | |
| 2011/0123083 A1 | 5/2011 | Ojha et al. | |
| 2013/0039558 A1* | 2/2013 | Balter | G06K 9/6289 382/131 |
| 2014/0221816 A1* | 8/2014 | Franke | G01R 33/4816 600/411 |

OTHER PUBLICATIONS

Eiber et al "Value of a Dixon'Based MR/PET Attenuation Correction Sequence for the Localization and Evaulation of Pet . . . " European Journal of Nuclear Medicine and Molecular Imaging, vol. 38, No. 9, Jun. 18, 2011 p. 1691-1701.

Zaidi et al "Magnetic Resonance Imaging Guided Attenuation and Scatter Corrections in Three-Dimensional Brain Positron Emission Tomography" Med. Phys. 30 (5) May 2003 p. 937-948.

Keereman et al, "MRI-Based Attenuation Correction for PET/MRI Using Ultrashort Echo Time Sequences" , The Journal of Nuclear Medicine, vol. 51, No. 5, May 2010, p. 812-818.

Vik et al "A New Method for Robust Organ Positioning in CT Images" ISBI Conference Publications 2912 p. 338-341.

Buerger et al Nonrigid Motion Modeling of the Liver from 3-D Undersampled Self-Gated Golden Radial Phase Encoded MRI, IEEE Transactions on Medical Imaging, vol. 31, No. 3, Mar. 2012 p. 805-815.

Berker et al, "MRI Based Attenuation Correction for Hybrid PET/MR Systems: A 4-Class Tissue . . . " The Journal of Nuclear Medicine, vol. 53, No. 5, May 2012 p. 796-804.

Kotys-Traughber et al "MR Cortical Bone Imaging Using UTE for Digitally Reconstructed Radiographs and Attenuation Correction . . . " Proc. Intl. Soc. Mag. Reson. Med. 20 (2012) p. 286.

Rahmer et al, "Merging UTE Imagine, Water-Fat Separation and T2 Mapping in a Single 3d MSK Scan" Proc. Intl. Soc. Mag. Reson. Med. 18 (2010) p. 3224.

* cited by examiner

DETECTION OF BONE TISSUE USING MAGNETIC RESONANCE IMAGING

CROSS REFERENCE TO RELATED APPLICATIONS

This application is a U.S. national phase application of International Application No. PCT/EP2014/056145, filed on Mar. 27, 2014, which claims the benefit of EP Application Serial No. 13161904.1 filed on Apr. 2, 2013 and is incorporated herein by reference.

TECHNICAL FIELD

The invention relates to magnetic resonance imaging, in particular to the detection or imaging of bone tissue.

BACKGROUND OF THE INVENTION

In Positron Emission Tomography (PET), and other nuclear medical imaging systems, the detection of 511 keV Gamma radiation caused by the decay of positron emitting radioisotopes with the body of a subject is reconstructed into an image. To perform this accurately it is beneficial to know the spatially dependent absorption of ionizing radiation within the subject.

Combined Computed Tomography (CT) and PET scanners have been constructed which use a low-dose CT to determine the attenuation factors at 511 keV. These scanners have the disadvantage of exposing subjects to radiation while performing a CT examination.

Combined Magnetic Resonance Imaging (MRI) and PET scanners have also been constructed. The journal article Eiber et. al. "Value of a Dixon-based MR/PET attenuation correction sequence for the localization and evaluation of PET-positive lesions" Eur J Nucl Med Mol Imaging (2011), vol. 38, pages 1691-1701, discloses the use of Dixon based MRI imaging techniques for attenuation correction for PET.

SUMMARY OF THE INVENTION

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three dimensional data that has been acquired using a medical imaging scanner. A medical imaging scanner is defined herein as an apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

Nuclear medical imaging data is another example of medical image data. Nuclear medical imaging data as used here encompasses the data recoded by a nuclear medical imaging system. Nuclear medical imaging data may be reconstructed into an image. A nuclear medical imaging system as used herein encompasses a medical imaging system that is operable to determine the spatially dependent concentration of radioisotopes within a subject by detecting the nuclear decay of the radioisotopes.

In one aspect the invention provides for a medical apparatus comprising a magnetic resonance imaging system for acquiring magnetic resonance data from an imaging zone. The medical apparatus further comprises a processor for controlling the medical apparatus. The medical apparatus further comprises a memory storing machine-executable instructions. Execution of the instructions cause the processor to acquire the magnetic resonance data using a pulse sequence which specifies an echo time greater than 400 µs. A pulse sequence as used herein is a sequence of commands which are performed in a particular sequence by the magnetic resonance imaging system in order to acquire the magnetic resonance data. The echo time is often abbreviated in the art as TE. The echo is essentially the radio signals received from the subject during the acquisition of the magnetic resonance data.

Execution of the instructions further causes the processor to reconstruct a magnetic resonance image using the magnetic resonance data. Execution of the instructions further cause the processor to generate a thresholded image by thresholding the magnetic resonance image in order to emphasize bone structures and to suppress tissue structures in the magnetic resonance image. Execution of the instructions further causes the processor to generate a bone-enhanced image by applying a background removal algorithm to the thresholded image. The use of a pulse sequence which specifies an echo time greater than 400 µs has the effect that bone structure does not generate a magnetic resonance image signal that is received during the echo. Bone structure will then appear as the same as the absence of tissue or outside of the subject during an image. Thresholding the image selects those areas which do not have a large MR signal coming from them. This would then include bone tissue and also air or regions outside of the subject. The background removal algorithm may then be used to remove areas which are for instance obviously outside of the subject. This embodiment may have the benefit of providing an easy and quick way of identifying possible locations of bone tissue.

In an embodiment the pulse sequence is a T1 weighted pulse sequence.

In another embodiment the pulse sequence is a T1 weighted Dixon pulse sequence. The magnetic resonance image is a so called in-phase image. This shows both water and fat tissue as being in phase with each other. Execution of the instructions further causes the processor to reconstruct a fat image and a water image from the magnetic resonance data. There are then three images, a fat image, a water image, and an in-phase image. These are typical to Dixon pulse sequences. Execution of the instructions further cause the processor to generate a tissue classification map using the fat image, the water image, and the bone-enhanced image. The Dixon method is useful for separating out fat and water images. When combined with the bone-enhanced image a map which effectively maps out mostly water, fat or bone tissue can be created.

In another embodiment execution of the instructions further cause the processor to generate a tissue map Digitally Reconstructed Radiograph (DRR) image by projecting the tissue classification map onto a chosen two-dimensional plane. The information about the location of bone, fat and water tissue is known three-dimensionally. However, physicians are accustomed to looking at X-ray type images. In this embodiment the three-dimensional data is projected onto a two-dimensional plane to make it easier for physicians or other healthcare professionals to interpret. In a variant of this embodiment the direct visual radiography image could be stored in a memory and/or displayed on a display.

In another embodiment execution of the instructions further cause the processor to generate an electron density map using the tissue classification map. This may for instance be useful for radiation therapy planning.

In another embodiment the medical apparatus further comprises a radiotherapy simulation system. Execution of the instructions further causes the processor to receive therapy parameters. The therapy parameters may for instance be a treatment plan or instructions developed by a physician or other healthcare professional to specify a portion of a subject to treat with radiotherapy. Execution of the instructions further cause the processor to generate a radiotherapy treatment plan using the radiotherapy simulation with the therapy parameters and the electron density map. This embodiment may be beneficial because the electron density map was created using knowledge of the actual fat, water and bone tissue within a subject. This may lead to the more accurate calculation of the electron density map and thereby a greater knowledge of how the attenuation of ionizing radiation will occur within the subject. This may result in a more accurate radiotherapy treatment plan for a subject.

In another embodiment the medical apparatus further comprises a nuclear medical imaging system integrated into the magnetic resonance imaging system. A nuclear medical imaging system as used herein is an imaging system which images the internal anatomy of a subject by detecting the decay of a radionuclide. Execution of the instructions further cause the processor to generate a spatially dependent tissue attenuation map descriptive of the attenuation of gamma radiation by the subject using the tissue classification map. A knowledge of the type of tissue can be used to determine how the tissue will attenuate the gamma radiation. Execution of the instructions further causes the processor to acquire nuclear medical imaging data using the nuclear medical imaging system. Execution of the instructions further causes the processor to reconstruct a nuclear medical image using the nuclear medical imaging data and the spatially dependent tissue attenuation map. The spatially dependent tissue attenuation map which was determined through the magnetic resonance imaging is used to more accurately construct the nuclear medical image.

In another embodiment the nuclear medical imaging system is a positron emission tomography system.

In another embodiment the nuclear medical imaging system is a single-photon emission computer tomography system.

In another embodiment execution of the instructions further causes the processor to apply a contrast inversion filter to the magnetic resonance image before generating the thresholded image. The bone tissue will generate only a noise signal and thus will have a much lower signal than for instance the water or fat tissue. By inverting it the noise becomes the larger signal and the water or fat tissue has a low signal. By then using a threshold which eliminates everything below a certain value the fat and water tissue are removed from the image leaving only noise and also bone tissue.

In another embodiment execution of the instructions further cause the processor to filter the bone-enhanced image using an anatomical atlas to remove artifacts. By using image processing techniques an anatomical atlas can be registered to the bone-enhanced image. It may also be registered to the unprocessed magnetic resonance image thereby creating a registration also to the bone-enhanced image. Once registered to the bone-enhanced image the anatomical atlas can be used to identify whether regions are likely bone tissue or likely not bone tissue. This may be used to more accurately discriminate between noise and bone tissue.

In another embodiment the anatomical atlas is a probabilistic atlas. By this a probabilistic atlas has the probability that each particular voxel is either bone tissue or not bone tissue. The bone-enhanced image is filtered by the anatomical atlas by registering the probabilistic atlas to the bone-enhanced image while after registration the atlas indicates a probability of a voxel in the bone-enhanced image as being bone or not being bone. Execution of the instructions further cause the processor to filter the bone-enhanced image by setting the voxel then in the bone-enhanced image to a predetermined value indicating no bone tissue if the probability is below the predetermined probability.

In another embodiment the anatomical atlas comprises a deformable model indicating locations of the bone tissue. In this embodiment the deformable model is a model which represents the typical anatomy which is expected of the subject. The model is then deformed or fitted to the actual bone-enhanced image or the magnetic resonance image. The model may then be used to directly check whether something is likely bone tissue or not bone tissue. Execution of the instructions further cause the processor to set the voxel in the bone-enhanced image to a predetermined value indicating no bone tissue if the voxel is outside the locations of the bone tissue specified by the deformable model.

In another embodiment execution of the instructions further cause the processor to generate a bone-enhanced digitally reconstructed radiograph (DRR) image by projecting the bone-enhanced image onto a selected two-dimensional plane. This embodiment may be beneficial because the three-dimensional bone-enhanced image is projected onto a plane which renders the data similar in form to that expected from a conventional X-ray. This may facilitate the use of the data by a physician or other healthcare provider to interpret the data in the bone-enhanced image properly. The DRR image could also for example be stored in memory and/or displayed on a display.

In another aspect the invention provides for a computer program product comprising machine-executable instructions for execution by a processor controlling the medical apparatus. The medical apparatus comprises a magnetic resonance imaging system for acquiring magnetic resonance data from an imaging zone. Execution of the instructions further causes the processor to acquire the magnetic resonance data using a pulse sequence which specifies an echo time greater than 400 μs. Execution of the instructions further causes the processor to reconstruct a magnetic resonance image using the magnetic resonance data. Execution of the instructions further cause the processor to generate a thresholded image by thresholding the magnetic resonance image to emphasize bone structures and suppressing tissue structures in the magnetic resonance image. Execution of the instructions further causes the processor to generate a bone-enhanced image by applying a background removal algorithm to the thresholded image.

In another aspect the invention provides for a medical apparatus comprising a processor for controlling the medical apparatus. The medical apparatus further comprises a memory for storing machine-executable instructions. Execution of the instructions further causes the processor to receive a medical image indicating the location of a specific tissue type. Execution of the instructions further causes the processor to register the medical image to an anatomical atlas indicating the location of the specific tissue type. Execution of the instructions further cause the processor to set a voxel in the medical image to a predetermined value indicating the absence of the specific tissue type. This is done if the voxel is outside the location of the specific tissue type.

In another embodiment the specific tissue type is bone tissue.

In another embodiment the medical apparatus further comprises a magnetic resonance imaging system for acquiring magnetic resonance data from an imaging zone. Execution of the instructions further cause the processor to acquire the magnetic resonance data using an ultrasound echo time pulse sequence. Execution of the instructions further cause the processor to reconstruct the medical image using the magnetic resonance data. In this embodiment an MRI system is used to acquire magnetic resonance data using a pulse sequence specifically designed for detecting bone or cortical bone tissue. The medical image is provided by the magnetic resonance imaging system. The medical image which may contain bone tissue is then filtered using the anatomical atlas to remove tissue which is in fact not bone tissue.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
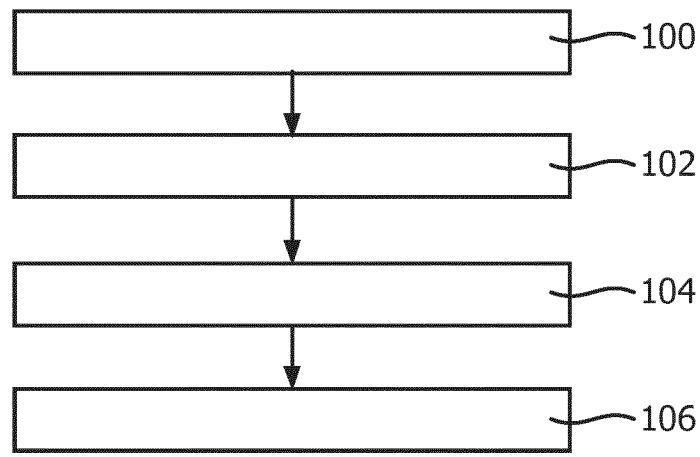
FIG. 1 shows a flowchart which illustrates a method.

FIG. 1 shows a flowchart which illustrates a method. In step 100 magnetic resonance data is acquired using the magnetic resonance imaging system with a pulse sequence which specifies an echo time greater than 400 μs. Next in step 102 a magnetic resonance image is reconstructed using the magnetic resonance data. Then in step 104 a thresholded image is generated by thresholding the magnetic resonance image to emphasize bone structures and suppressing tissue structures in the magnetic resonance image. Before a thresholding image other pre-processing steps such as inverting the image may also be performed. Finally in step 106 a bone-enhanced image is generated by applying a background removal algorithm to the thresholded image. For instance the background removal algorithm could remove portions of the image which are obviously noise or not bone tissue. For instance regions outside of the subject will also generate noise that would resemble the signal from bone.

Figure 2:
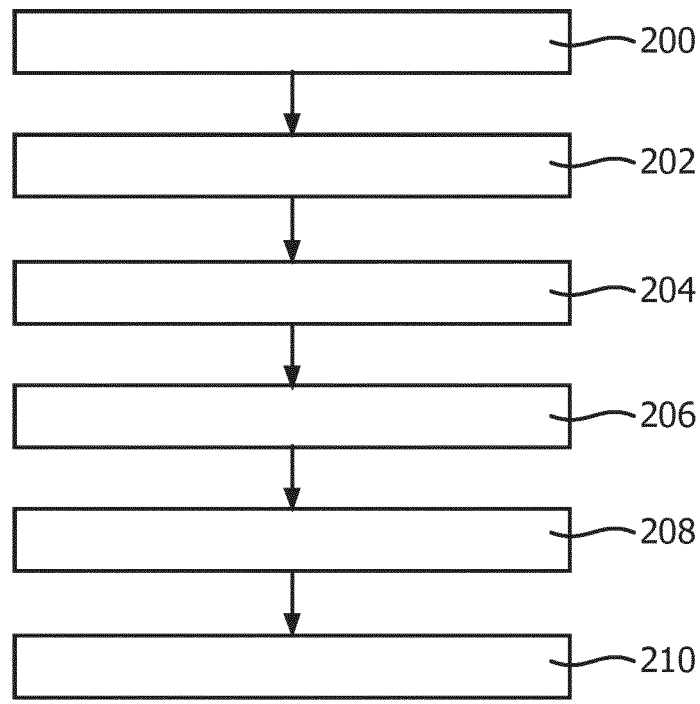
FIG. 2 shows a flowchart which illustrates a further method.

FIG. 2 shows a flowchart which illustrates a further example of a method. Step 200 is the same as step 100. Next step 202 is also the same as step 102 in FIG. 1. Step 204 is the same as step 104 in FIG. 1 and step 206 is the same as step 106 in FIG. 1. The magnetic resonance image is a T1 weighted image which is a so called in-phase image. It shows both the water and the fat signal. The next step is step 208 and this is to reconstruct a fat image and a water image from the magnetic resonance data. The pulse sequence used to acquire the magnetic resonance data is a T1 weighted Dixon pulse sequence. Finally in step 210 a tissue classification map is generated using the fat image, the water image and the bone-enhanced image.

Figure 3:
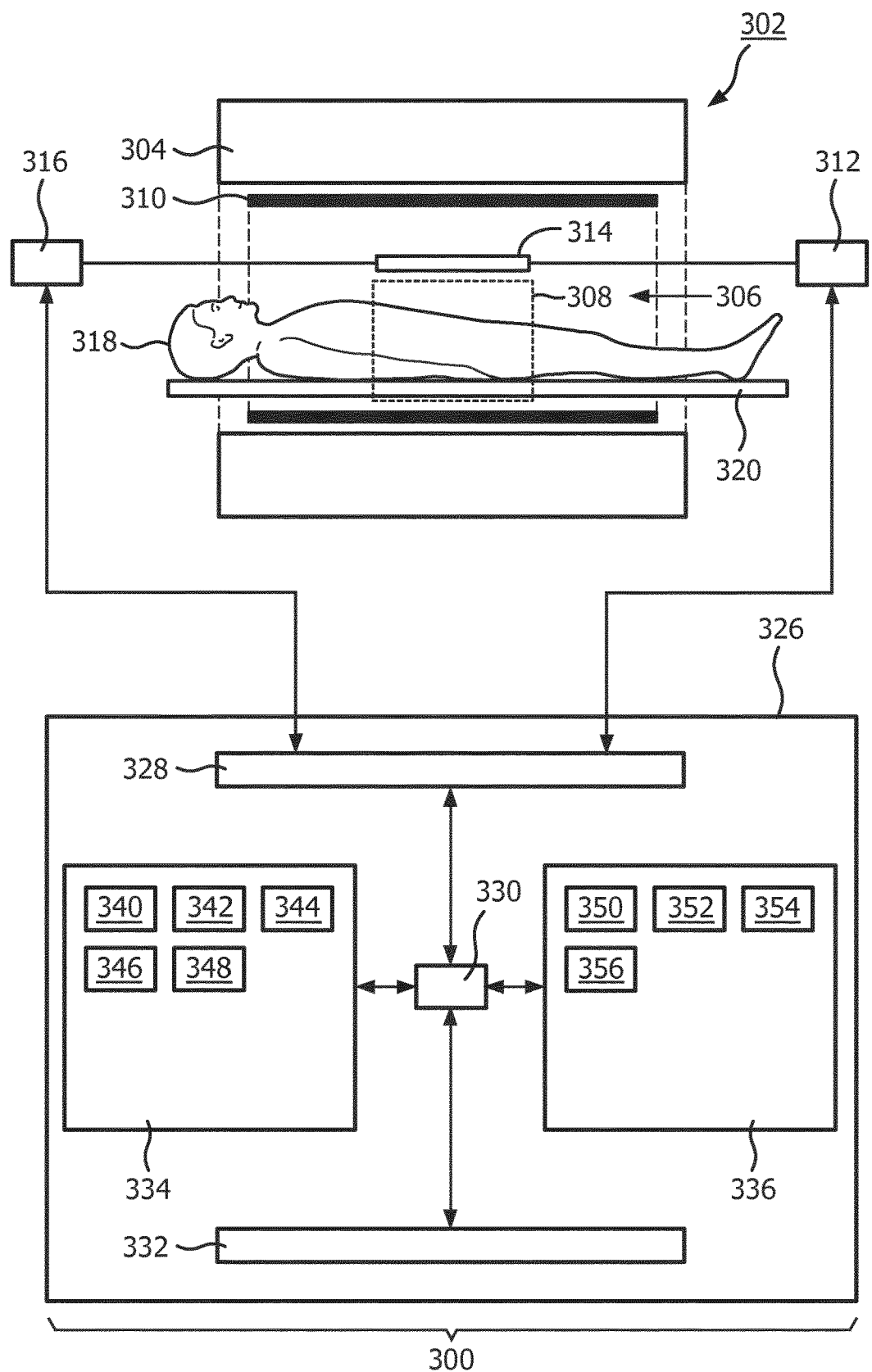
FIG. 3 illustrates an example of a medical instrument.

FIG. 3 shows an example of the medical apparatus 300. The medical apparatus 300 comprises a magnetic resonance imaging system 302. The magnetic resonance imaging system 302 comprises a magnet 304. The magnet 304 is a superconducting cylindrical type magnet 304 with a bore 306 through it. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet 304 there is an imaging zone 308 where the magnetic field is strong and uniform enough to perform magnetic resonance imaging.

Within the bore 306 of the magnet there is also a set of magnetic field gradient coils 310 which is used for acquisition of magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers.

The magnetic field gradient coil power supply 312 and the transceiver 316 are connected to a hardware interface 328 of computer system 326. The computer system 326 further comprises a processor 330. The processor 330 is connected to the hardware interface 428, a user interface 432, computer storage 334, and computer memory 336.

The computer storage 334 is shown as containing a pulse sequence 340. The pulse sequence specifies an echo time greater than 400 µs. The computer storage 334 further shows magnetic resonance data 342 that has been acquired using the pulse sequence 340. The computer storage 334 further shows a magnetic resonance image 344 which has been reconstructed from the magnetic resonance data 342. The computer storage 334 further shows a thresholded image 346 that has been generated from the magnetic resonance image 344 by thresholding it and possibly performing other image processing tasks before thresholding. The computer storage 334 is shown as further containing a bone-enhanced image 348 that was produced from the thresholded image 346.

The computer memory 336 is shown as containing a control module. The control module contains computer-executable code which enables the processor 330 to control the operation of the medial apparatus 300. The control module 350 for instance enables the processor 330 to control the magnetic resonance imaging system 302 via the hardware interface 328 to acquire the magnetic resonance data 342. The computer memory is further shown as containing image reconstruction module 352. The image reconstruction module 352 is able to reconstruct magnetic resonance images 344 from magnetic resonance data 342. The computer memory 336 is further shown as containing an image processing module 354. The image processing module 354 enables the processor 330 to perform basic image processing techniques such as inverting the image, taking a threshold of an image and also combining various types of image data together. The computer memory 336 is further shown as containing a background removal module 356. This is custom computer code which enables the processor 330 to process the thresholded image 346 to produce the bone-enhanced image 348.

Figure 4:
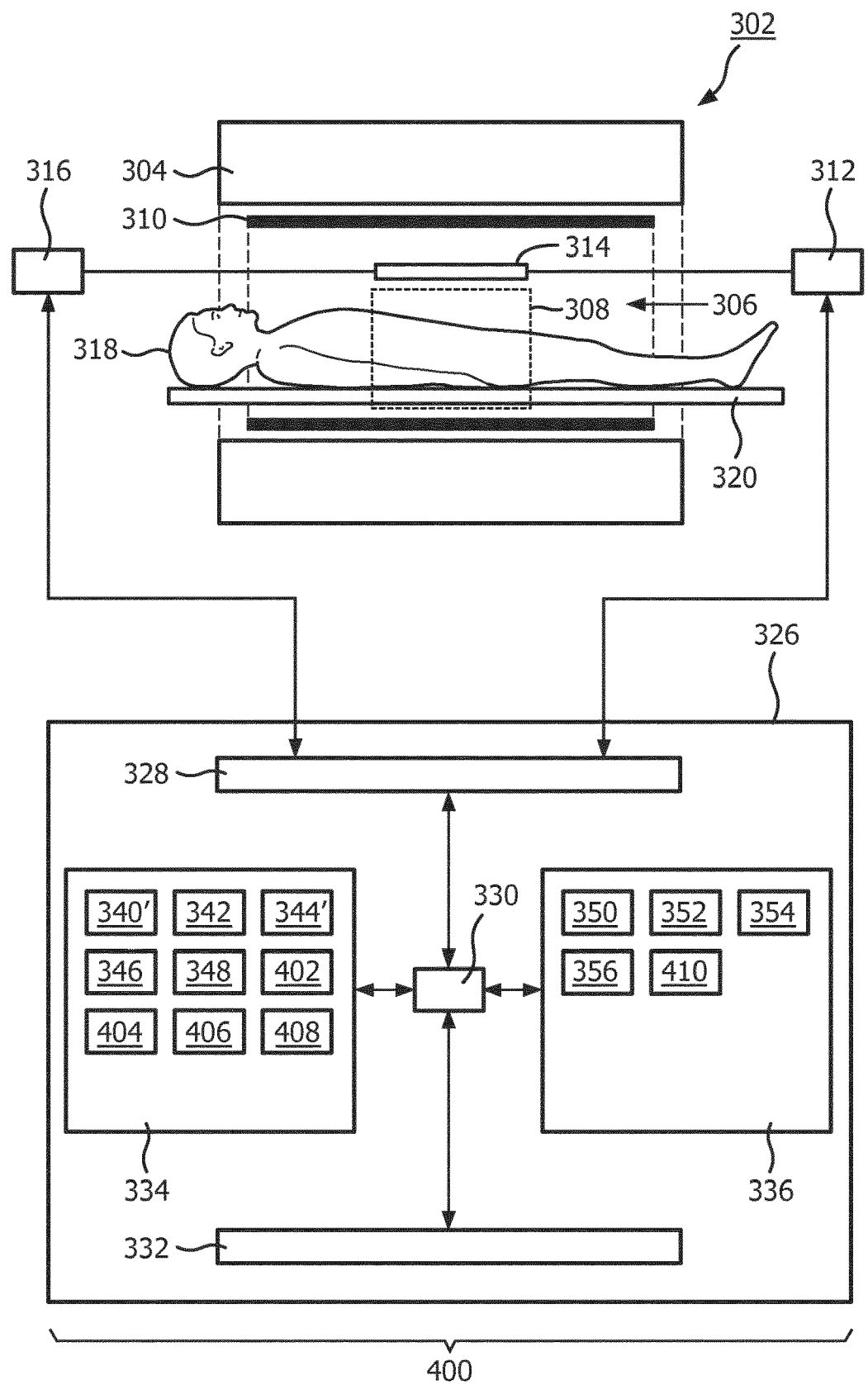
FIG. 4 illustrates a further example of a medical instrument.

FIG. 4 shows a medical apparatus 400 similar to that shown in FIG. 3. In the example shown in FIG. 4 the pulse sequence 340' is a T1 weighted Dixon pulse sequence instead of a pulse sequence which specifies an echo time greater than 400 µs. The magnetic resonance image 344' is a so called in-phase image as opposed to just simply a magnetic resonance image as is shown in FIG. 3. The image reconstruction module 352 was used to process the magnetic resonance data 342 to generate a fat image 402 and a water image 404 from the magnetic resonance data also. The computer memory 334 is also shown as containing a tissue classification map 406 which was constructed by combining the fat image 402, the water image 404, and the bone-enhanced image 348. The computer storage 334 also shows an example of a DDR image. This for instance is a 2D projection of the tissue classification map 406 or the bone-enhanced image 348. The DDR image 408 may be displayed on the user interface 332. The computer memory is shown as further containing an anatomical atlas image filter module 410. The anatomical atlas image filter module in this example uses an anatomical atlas in conjunction with image processing techniques to remove bone that is not really bone from the bone-enhanced image 348.

Figure 5:
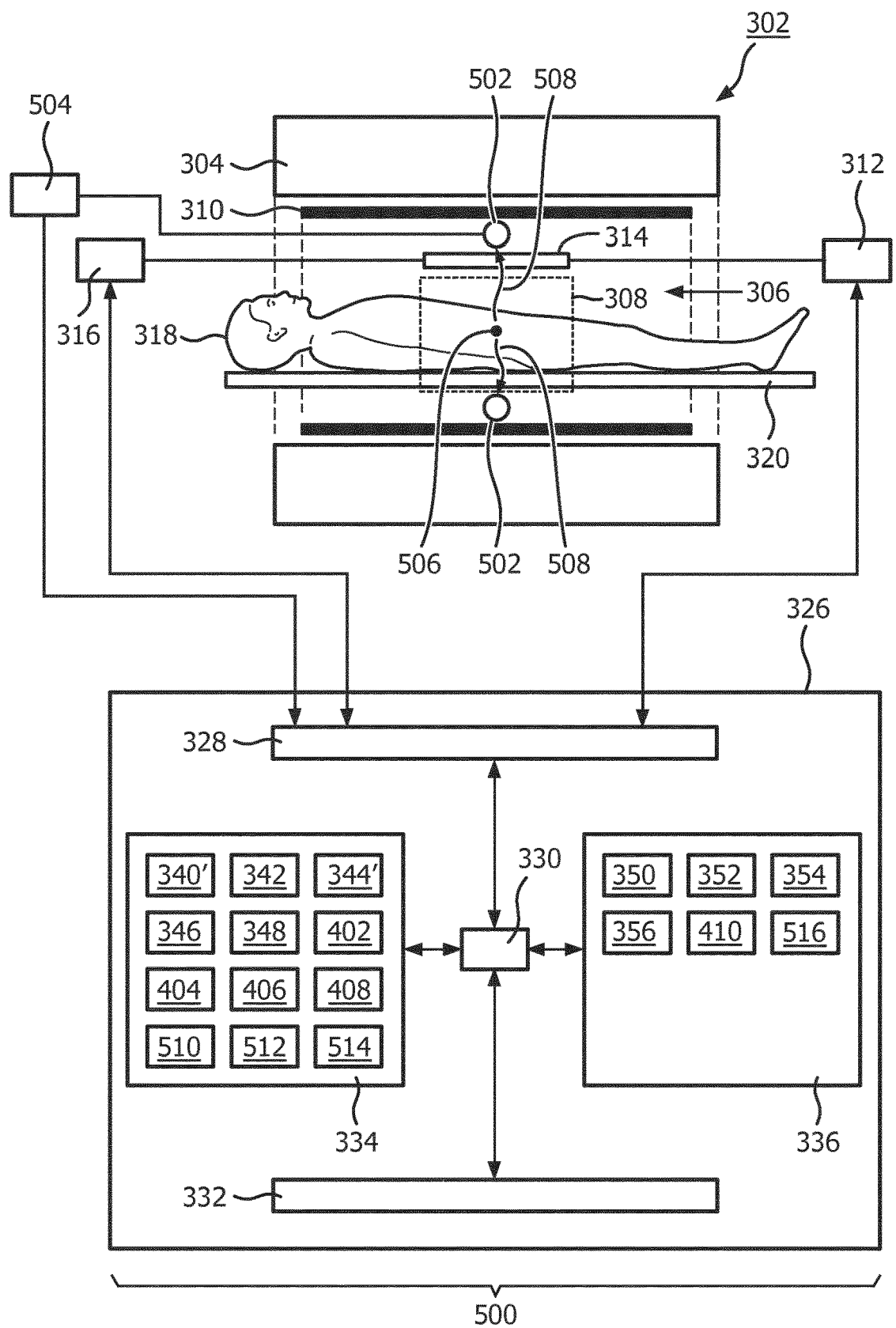
FIG. 5 illustrates a further example of a medical instrument.

FIG. 5 shows a further example of a medical apparatus 500. The medical apparatus shown in FIG. 5 is similar to that shown in FIG. 4 with the exception that there has been a nuclear medical imaging detector 502 and electronics 504 which have been added. The electronics are connected to the hardware interface 328. The detector 502 and electronics 504 are intended to be representative and may for instance be a positron emission tomography system or a SPECT system. The detector 502 for instance may be a ring of scintillators with columators, and which have fiber optics or other pipes for bringing light generated by the scintillators to the electronics 504. The computer storage 334 is shown as additionally containing a spatially dependent tissue attenuation map 510 that was calculated using a tissue classification map 406. The computer memory 336 contains a tissue attenuation map generation module 516 that was used for this.

The computer memory 334 is further shown as containing nuclear medical imaging data 512 that was acquired from the nuclear medical imaging electronics 504. For instance when a radionuclide 506 within the subject 318 decays photons or gamma radiation 508 may be emitted and detected by the detectors 502. The computer storage 334 is further shown as containing a nuclear medical image 514 that was reconstructed by the image reconstruction module 352 using the nuclear medical imaging data 512 and the spatially dependent tissue attenuation map 510.

Conventional density maps are usually derived from computed tomography (CT) scans which expose the subject to a large amount of ionizing radiation. On the other hand, emerging applications based on magnetic resonance imaging (MRI), such as radiation therapy planning (RTP) and hybrid PET/MR systems, benefit from the superior display of soft tissue contrast. However, so far MRI has not been utilized for standalone radiation therapy simulation since this would require segmentation of cortical bone. Conventional MRI sequences cannot reliably detect cortical bone due to the fast T2 decay.

Examples of the medical instrument may provide a new approach on the basis of a T1-weighted Dixon acquisition and reconstruction workflow for tissue classification and cortical bone imaging. Subsequently these images can be used to generate density maps and digitally reconstructed radiographs (DRRs).

Emerging applications based on magnetic resonance imaging (MRI), such as radiation therapy planning (RTP) and hybrid PET/MR systems, benefit from the superior display of soft tissue contrast and the delineation of tumor and critical organs. However, so far MRI has not been utilized for standalone radiation therapy simulation since this would require the generation of electron density (ED) maps as well as segmentation of cortical bone for the creation of digitally reconstructed radiographs (DRRs) in order to perform 2D patient matching. It has been demonstrated that the inherent lack of electron density information in MR images might be overcome by tissue classification on the basis of Dixon MR techniques and subsequent bulk electron density assignment.

Conventional density maps are usually derived from computed tomography (CT) scans which expose the subject to a large amount of ionizing radiation. In order to minimize the dose of ionizing radiation during a single measurement, CT-derived density maps are commonly single shot helical CT scans that can suffer from respiratory motion and may result in blurred images or that only reflect a certain point in the respiratory cycle. This can lead to a mismatch in the measured PET emission distribution leading to image artifacts in the reconstructed PET images.

For RTP it has become necessary to visualize a certain anatomy in three dimensions which makes it possible to conform the dose around the target volume in order to irradiate the tumor to as high a dose as possible, whilst saving normal tissues. From CT images alone this can be hard to achieve due to the reduced soft tissue contrast which often requires other imaging modalities like MRI or PET, however, problems can occur when these images are co-registered to CT in order to maintain geometric accuracy.

Conventional MRI sequences cannot reliably detect cortical bone due to the fast T2 decay. Promising results were obtained with 3D ultrashort echo time imaging (UTE) in the knee as well as in the head. However, UTE bone imaging in other regions of the body, e.g. in the pelvis, is more demanding due to the significantly larger field-of-view (FOV). Moreover, images acquired with the UTE approach can present additional artifacts, which might arise from residual signal of ultra-short T2-components of the skin, but also from eddy current related trajectory errors.

Examples of the medical apparatus may provide a new means using T1-weighted Dixon acquisition (or other MR acquisition techniques) and reconstruction workflow for tissue classification and cortical bone imaging. Subsequently these images can be used to generate (electron) density maps or for calculation of attenuation as well as for generating DRRs.

In examples of medical apparatus, the data acquisition may be achieved with a clinical MRI system using the body coil for transmission, and, for instance, a 12-element phased-array posterior coil and a 16-element phased-array anterior coil for signal reception. A T1-enhanced 3D Cartesian fast-field echo acquisition is employed, acquiring two signal echoes with the magnetization nearly out-phase at TE1=1.1 ms and nearly in-phase at TE2=2.1 ms. Other imaging parameters can be e.g. repetition time TR=3.3 ms, flip angle $\alpha=10°$, voxel size $1.7\times1.7\times2.5$ mm$^3$, FOV $300\times400\times350$ mm$^3$.

Figure 6:
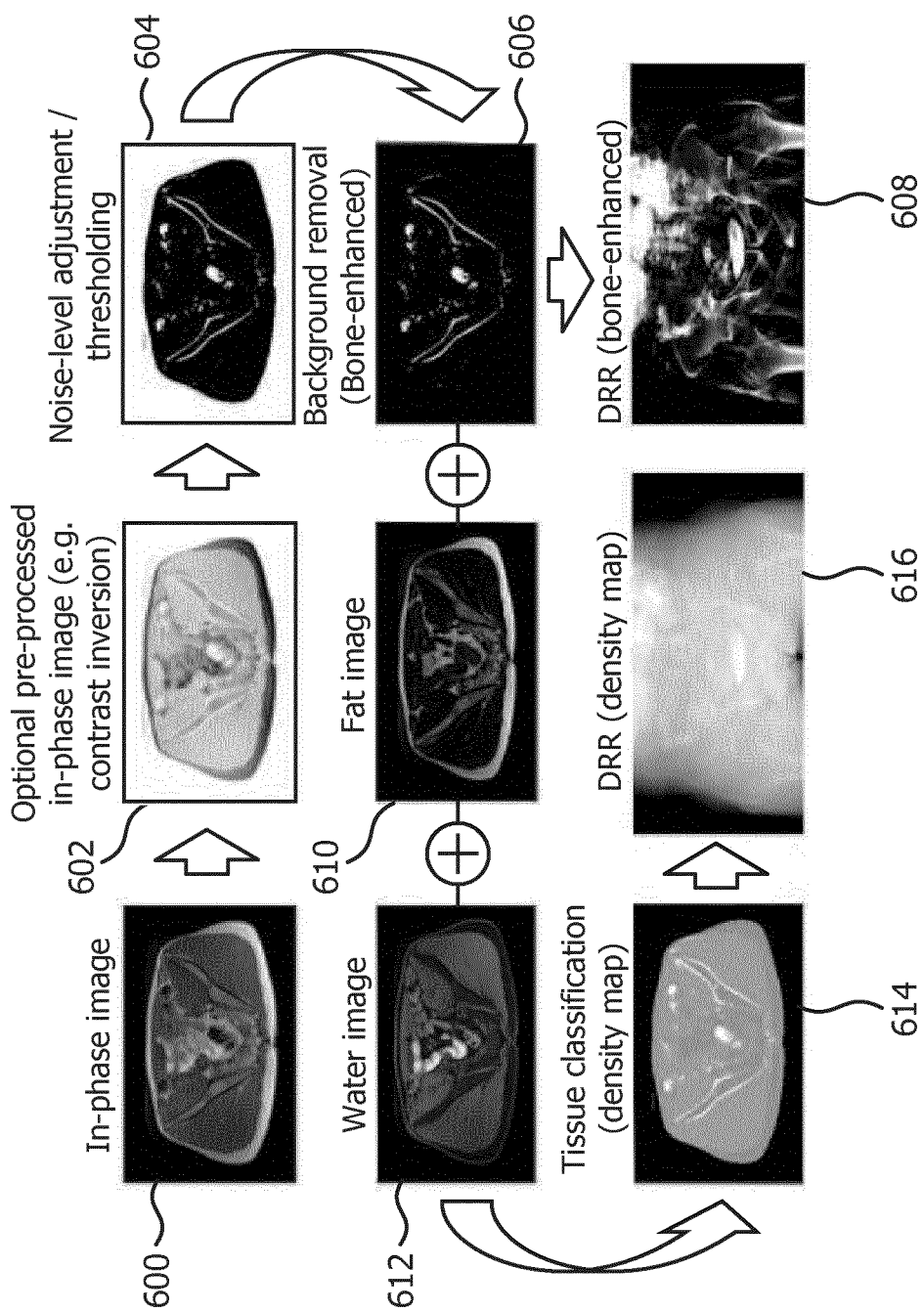
FIG. 6 shows an example of a workflow for generating bone-enhanced images and tissue classification from a T1 Dixon pulse sequence.

FIG. 6 shows an example of a workflow for generating bone-enhanced images and tissue classification from a T1 Dixon pulse sequence. In the T1 Dixon sequence an in-phase image which shows the combination of water and fat is reconstructed as well as a water image and a fat image. The method starts showing an example of an in-phase image 600. Next in step 602 optional pre-processing on the in-phase image is performed. For example a contrast inversion is performed. The contract inversion makes all of the dark areas which would be air pockets, noise from areas outside of the subject and also bone tissue would become very light instead of dark. Next in step 604 a thresholding of the image is performed. This effectively eliminates all the fat and water tissue regions from the image. Next in step 606 background removal is performed. For example in the periphery of the subject there is a region which is obviously not bone tissue because it is outside of the subject. This may easily be removed using a suitable algorithm. The bone-enhanced image 606 is essentially a three-dimensional spatial image particularly if more than one slice is involved. This may be projected onto a two-dimensional plane to produce for example a DRR bone-enhanced image. An example is shown in image 608. The bone-enhanced image 608 may also be combined with a water image 612 and a fat image 610 to generate a tissue classification or density map 614. A tissue classification map 614 may also be projected onto a two-dimensional plane to generate a DRR density map 616.

Reconstruction workflow for tissue classification and bone-enhancement (FIG. 6):

0. Optional pre-processing of the acquired in-phase images (TE2), e.g. image smoothing, contrast inversion etc.
1. A mask is generated from the original or from the pre-processed in-phase images by adjusting and thresholding the noise level in such a way that bone structures are visible and surrounding tissue is being suppressed.
2. Background signal is removed, e.g. by employing a region growing algorithm. This results in pure bone-enhanced images.
3. Water and fat fractions are derived from a conventional Dixon reconstruction of the nearly in-phase (TE2) and out-phase images (TE1).
4. Density maps can be generated by encoding the classified voxels with known attenuation values of soft tissue (water), adipose tissue (fat), and bone and combining them into one image.
5. DRRs can be reconstructed from both the bone-enhanced images as well as from the density maps.

As described above, bone-enhanced images and tissue classification may allow generating density maps that can be used for calculation of attenuation of photon (6-15 MeV) or electron (4-20 MeV) energies and that are mainly applied in radiation therapy. However, density maps can also be used for calculation of attenuation of 511 KeV which can be applied for attenuation correction in PET/MR systems.

Figure 7:
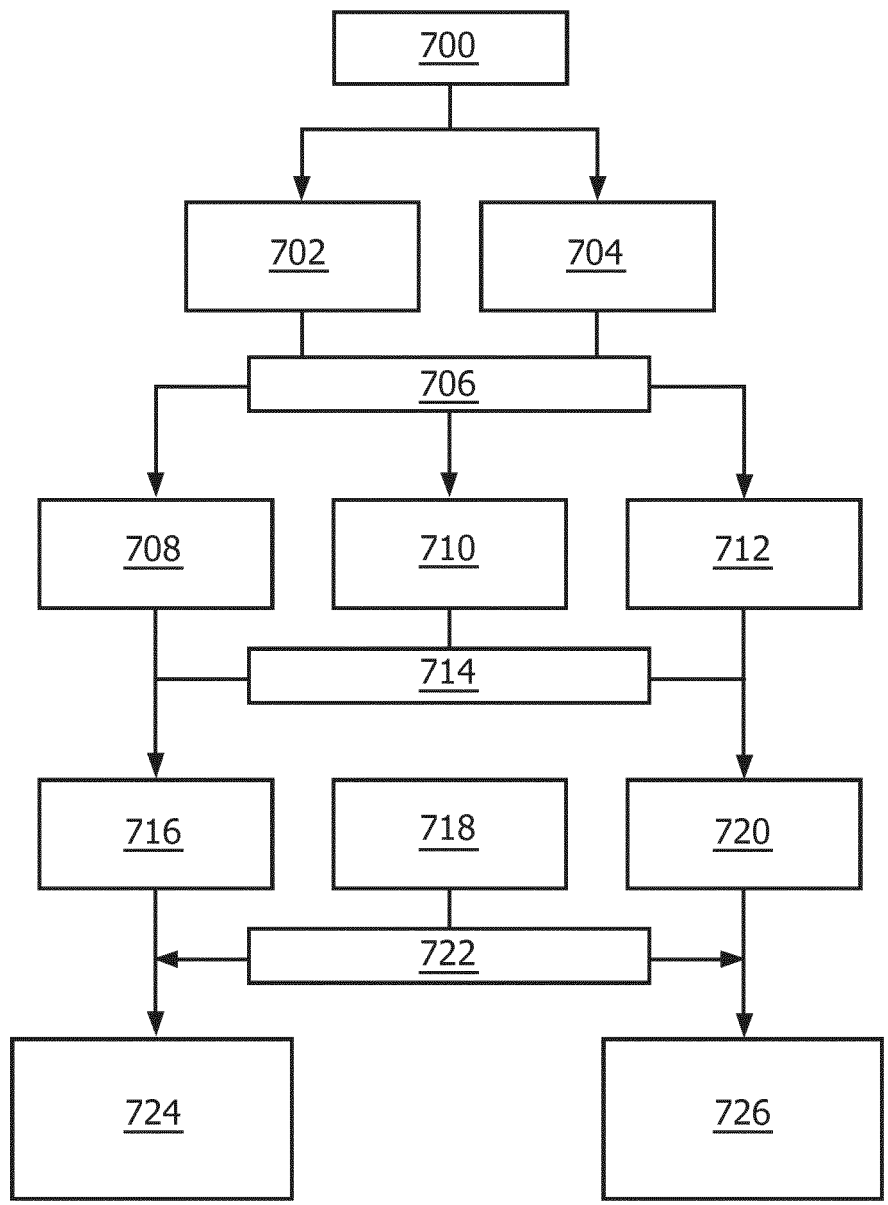
FIG. 7 shows a workflow of how to generate electron density maps and DRRs using only magnetic resonance imaging.

FIG. 7 shows a workflow of how to generate electron density maps and digitally reconstructed radiographs or DRRs based on magnetic resonance imaging solely. First in step 700 magnetic resonance image acquisition is performed using a Dixon method. This results in image 702 and 704 from the first and second echoes respectively. Next a Dixon reconstruction 706 is performed. This yields an in-phase image 708, a water image 710 and a fat image 712. Next in step 714 tissue classification and electron bulk density assignment is performed using these three images. For example a bone-enhanced image 716 may be generated as described previously and also an electron density map 720 may also be generated. 718 represents a bone probability atlas. 722 represents the step of filtering the images 716 and 720 using the bone probability atlas. This yields a filtered bone-enhanced image 724 and a filtered electron density map 726. The images 724 and 726 can then be projected onto two-dimensional planes to construct DRR images.

Figure 8:
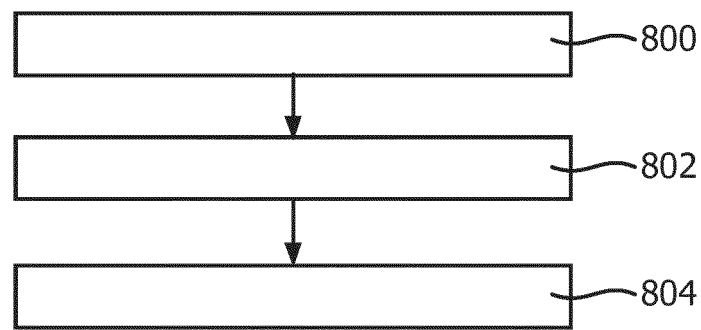
FIG. 8 shows a flowchart which illustrates a further method.

FIG. 8 shows a flow diagram which illustrates a method. In step 800 a medical image is received which indicates the location of a specific tissue type. Next in step 802 the medical image is registered to an anatomical atlas indicating the location of this specific tissue type. For instance the anatomical atlas may be a deformable model or it may also indicate the probability that a particular voxel or pixel contains the specific tissue type. Finally in step 804 a voxel in the medical image is set to a predetermined value indicating the absence of the specific tissue type if the voxel is outside of the location of the specific tissue type as indicated by the anatomical atlas.

In the method shown in FIG. 8 the "specific tissue type" may for instance be replaced with the phrase "bone tissue."

Figure 9:
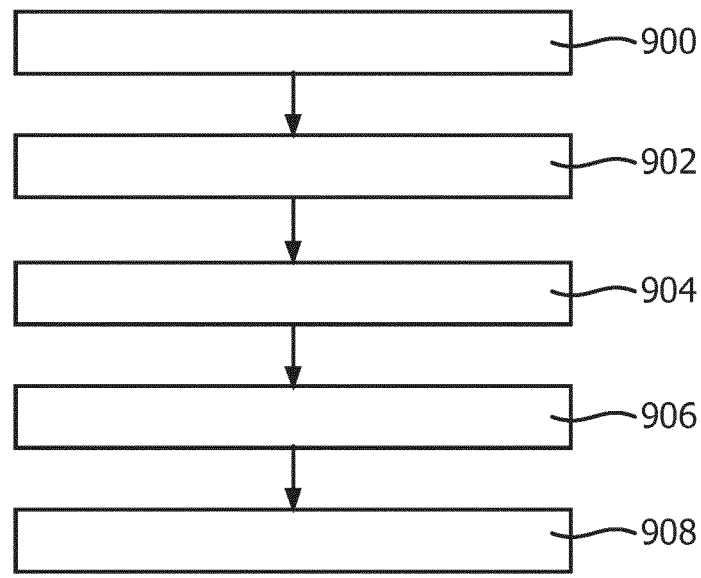
FIG. 9 shows a flowchart which illustrates a further method.

FIG. 9 shows a flow diagram which illustrates a further method. First in step 900 bone magnetic resonance data is acquired using an ultra short echo time pulse sequence. An ultra short echo time pulse sequence may for instance be a pulse sequence which has an echo time less than 400 μs. The ultra short echo time pulse sequence is useful for imaging bone tissue.

Next in step 902 a medical image is reconstructed using the ultra short echo time pulse sequence. The medical image is essentially a magnetic resonance image of bone tissue in a subject. Next in step 906 the medical image is received by a processor. The medical image indicates the location of bone tissue. Next in step 904 the medical image is registered to an anatomical atlas indicative of the location of bone tissue. Then finally in step 908 a voxel in the medical image is set to a predetermined value if that voxel indicates bone tissue but the anatomical atlas indicates that a voxel does not contain bone tissue or likely does not contain bone tissue.

Figure 10:
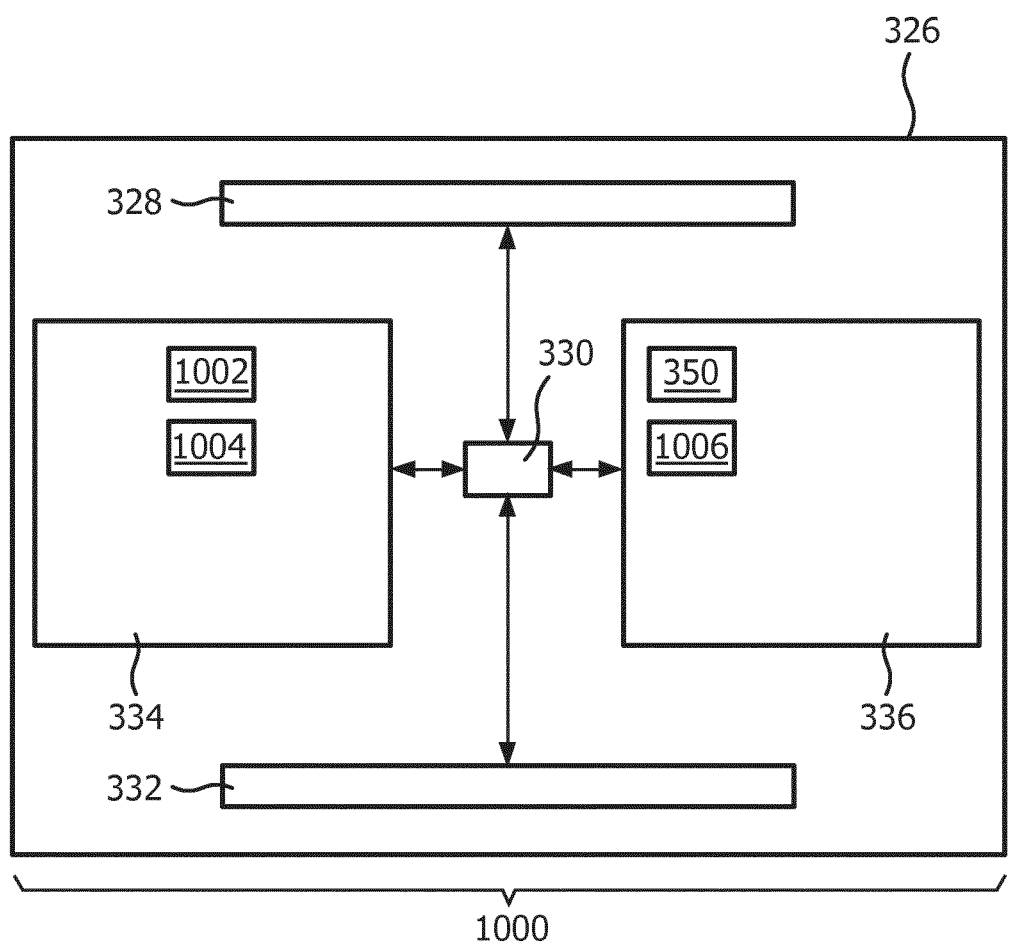
FIG. 10 illustrates a further example of a medical instrument.

FIG. 10 shows an example of a medical apparatus 1000. The medical apparatus 1000 shown in FIG. 10 comprises a computer 326 similar to the computer 326 in FIG. 3. The computer storage 334 is shown as containing a medical image. The medical image indicates the location of a specific tissue type. The computer storage 334 also shows a filtered medical image 1004. The computer memory 336 contains an anatomical atlas-based filter module 1006 which was used to generate the filtered medical image 1004 from the medical image 1002. The module 1006 registers the medical image to an anatomical atlas indicating the location of the specific tissue type. Then a voxel in the medical image is set to a predetermined value indicating the absence of the specific tissue type. This may be repeated for many voxels within the medical image to essentially filter the entire image.

Figure 11:
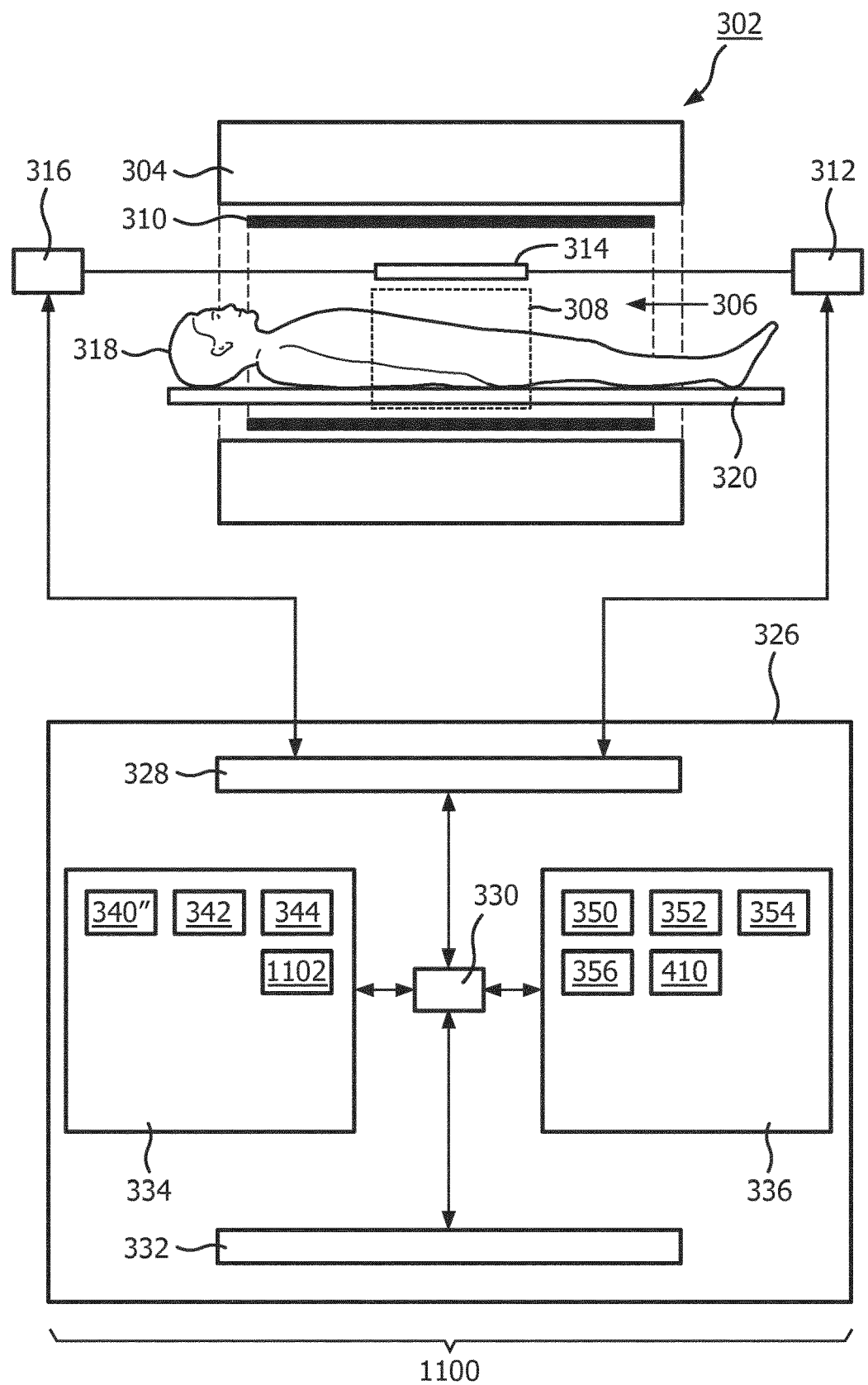
FIG. 11 illustrates a further example of a medical instrument.

FIG. 11 shows an example of a medical instrument 1100. The medical instrument shown in FIG. 11 is similar to that shown in FIG. 4. The difference is that the pulse sequence 340" is an ultra short echo time pulse sequence. The magnetic resonance data 342 was acquired using the pulse sequence 340" and the magnetic resonance image 344 that was reconstructed from the magnetic resonance data 342 shows the location of bone tissue. The anatomical atlas image filter module 410 is still present in the computer memory 336. The module 410 was then used to filter the magnetic resonance image 344 to generate a filtered image 1102. The thresholded image 346 and bone-enhanced image 348 of FIG. 4 are not present in the embodiment shown in FIG. 11.

Generation of maps related to electron density from Magnetic Resonance (MR) images is a topic of great interest e.g. for PET attenuation correction for integrated PET/MR scanner systems or for the simulation of radiation therapy, which is one step in the radiation therapy planning process. A key problem in that process stems from the fact that there is in general no clear correlation between the electron density of a material and its imaging properties in MR, e.g. both air and bone (i.e. materials with very different electron densities) usually show up with very low intensities in MR images. One approach pursued in the academic world to alleviate the problem is to use Ultrashort Echo-Time imaging (UTE), a technique that is known to produce some signal intensity from bone areas. This approach is known to work reasonably well for the head; however it still produces substantial artifacts in particular in the abdominal body region.

Figure 13:
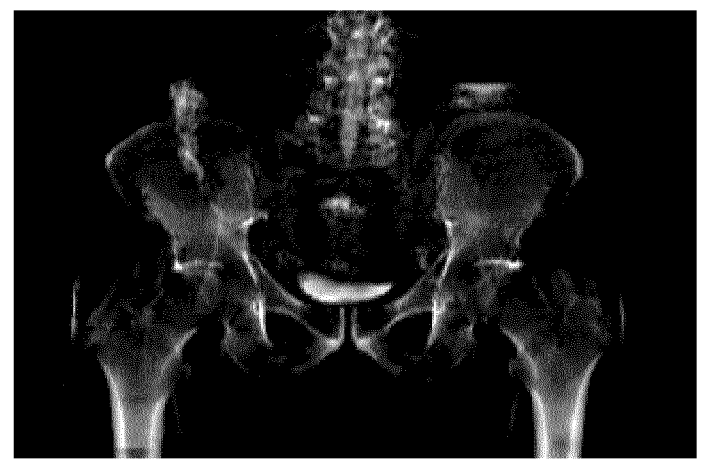
FIG. 13 shows a DDR using the same data as for FIG. 12 except artifact detection and elimination using an anatomical filter has been performed.

Examples of a method for the reduction of those artifacts is disclosed. An intensity-based mapping of the MR image intensities to electron density values produces a substantial number of voxels that are falsely assigned bone electron density values due to the partial volume effect and due to the physical properties of the material (e.g. bowel contents); see the left image below. Those "false positive" voxels can be eliminated by image processing methods, which are currently used for the automatic structure segmentation on CT images for the purpose of radiation therapy planning One such method is the adaptation of a probabilistic atlas of the bone structures to the (converted) MR images; all potential bone voxels where the respective probability as estimated from the atlas is below a certain threshold could be eliminated, greatly improving the classification, as shown in FIG. 13.

This method is not restricted to UTE images; other MR imaging techniques (e.g. Dixon images) suffer from the same problem. This method may also be applied to these other imaging techniques.

Generation of maps related to electron density from Magnetic Resonance (MR) images is a topic of great interest in various fields. For example, for the attenuation correction within the PET reconstruction on integrated PET/MR scanner systems it is essential to have a map of the photon attenuation of the object in the scanner at 511 keV, which needs to be derived from the respective MR image. As another example, for the simulation of a radiation therapy, which is one step in the radiation therapy planning process, it would also be in some cases highly beneficial if the CT scan (which is currently used for the simulation) could be replaced by an MR scan. In this scenario, the x-ray attenuation and scatter properties of the material at the 1-10 MeV range have to be estimated, which is also related to the electron density.

A key problem in the estimation of bulk electron density from MR images stems from the fact that there is in general no clear correlation between the electron density of a material and its imaging properties in MR. For example, both air and bone (i.e. materials with very different electron densities) usually show up with very low intensities in MR images. There are several approaches described in the literature that use certain segmentation techniques in order to discriminate between air an bone; however most of these approaches are described only for the head.

One approach pursued in the academic world to alleviate the problem is to use Ultrashort Echo-Time imaging (UTE), a technique that is known to produce some signal intensity from bone areas. In combination with another MR imaging sequence (e.g. T2w) this in theory allows for a discrimination between air and bone voxels just based on the local image intensities, without the need for additional segmentation or classification algorithms. This approach is known to work reasonably well for the head; however it still produces substantial artifacts in particular in the abdominal body region. The physical reason for those artifacts is that there is other material within the body (bowel contents) that has a T1 decay behavior very similar to that of bone; since both types of material (bowel contents and cortical bone) don't give a usable MR signal with other known imaging methods, they are not distinguishable by any combination of UTE with other MR imaging methods just based on the intensity alone.

Figure 12:
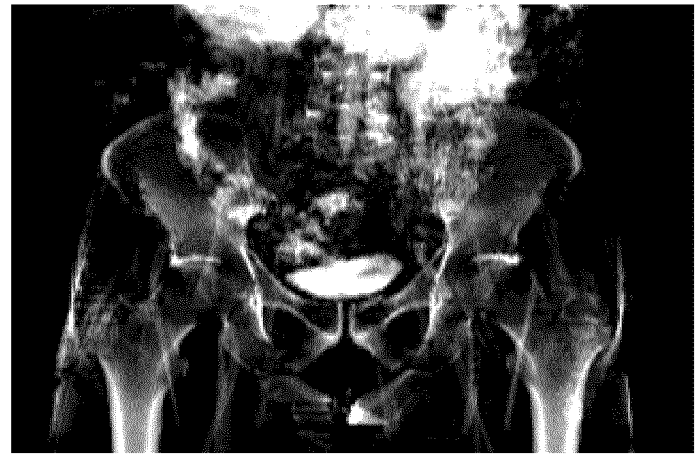
FIG. 12 shows a DRR of a magnetic resonance-based electron density map.

FIG. 12 shows a digitally reconstructed radiograph or DRR of a magnetic resonance-based electron density map using a voxel-by-voxel intensity-based mapping. It can be noticed that in the area around the spine there are several light areas and also in the region of the intestines may indicate the presence of air within the subject.

FIG. 13 shows the same data used to generate a digitally reconstructed radiograph except artifact detection and elimination using the anatomical filtering has been performed. It can be seen that the DRR image in FIG. 13 shows many fewer artifacts than shown in FIG. 12.

Examples of a medical instrument for the reduction of those artifacts are disclosed. A mapping of the MR image intensities to electron density values just based on the individual intensity values produces a substantial number of voxels that are falsely assigned bone electron density values due to the partial volume effect and due to the physical properties of the material (e.g. bowel contents); cf. FIG. 12. Those "false positive" voxels can be eliminated by image processing methods, which are currently used for the automatic structure segmentation on CT images for the purpose of radiation therapy planning One such method is the adaptation of a probabilistic atlas of the bone structures to the (converted) MR images; all potential bone voxels where the respective probability as estimated from the atlas is below a certain threshold could be eliminated, greatly improving the classification, as shown FIG. 13.

Note that with this method, organ probabilities (i.e. probabilities for a voxel to belong to a specific anatomical organ) learned from CT can be carried over to another modality, given that there is a registration algorithm available. The registration in the example of the creation of electron density maps from UTE MR images can even be accomplished in various ways, either by a direct registration of the CT-based atlas onto the MR images using a multi-modal registration, or (as described) by first mapping the voxels of the MR image onto a CT-like intensity scale and then using a mono-modal registration, assuming that the artifacts do not prevent the registration from working properly.

In a typical embodiment of the invention one would start with a UTE image along with a conventional (e.g. T2-weighted) image of a patient. Based on those two images, CT intensity values ("Hounsfield"-values) are assigned to the individual voxels. This is done on a voxel-by-voxel basis, i.e. if both the UTE and the conventional MR image show low intensities, the voxel is assigned an "air" value; if the UTE image shows some significant value, where the conventional MR image shows very low intensity, the voxel is assigned a "bone" CT value, and if both images show significant intensities, the voxel is assigned a "soft tissue" CT value. This constitutes a "pseudo CT image", i.e. a mapped image with a CT-like intensity distribution. The drawback however is that this mapping usually suffers from severe artifacts, i.e. generally a substantial number of voxels is misclassified due to the partial volume effect and due to the physical properties of the images material (e.g. bowel contents has the same relaxation properties as bone, so in this scheme it will lead to substantial artifacts in the bowel area).

However, for these "pseudo CT images" the image processing technology developed for CT images is applicable. In particular the probabilistic segmentation method, which was developed as a preprocessing step for image segmentation of CT images in radiation therapy planning, can be applied. This method basically registers an atlas containing organ probabilities onto a particular dataset, thus mapping those organ probabilities onto the dataset. If this technique with an atlas denoting bone probabilities is applied to the "pseudo CT images", the resulting "bone probability" can be used to identify and subsequently eliminate artifacts, e.g. by applying some probability threshold (e.g. if a voxel is classified as bone, but has a bone probability according to the mapped atlas below some threshold, e.g. 0.02, then it is considered an artifact and assigned a "soft tissue" CT value).

It should be noted however that this method is not restricted to UTE images. For instance, a voxel-by-voxel mapping scheme could also be applied to Dixon or mDixon MR images, where the soft tissue is classified based on the intensities of the water and fat image, respectively; generally bone and air are not distinguishable by this method, so that again a large number of voxels are misclassified. By applying the probabilistic segmentation technique, the number of misclassified voxels can also be dramatically reduced.

The probabilistic segmentation is one particular technique that can be used for the purpose of artifact reduction; other methods inferring prior knowledge (usually expressed in a model) onto an image of classified voxels are also applicable for this purpose. This method is limited however to body areas with a clear and visible distinction between the different compartments, since otherwise the registration of the model onto the dataset will not be sufficiently accurate, or the model itself might not be sufficiently sharp (i.e. there might be a large number of voxels with a relatively high probability for both air and bone, making an assignment based on those probabilities error prone). Thus this method might not work e.g. on head images, where bone and air areas are in close proximity.

Figure 14:
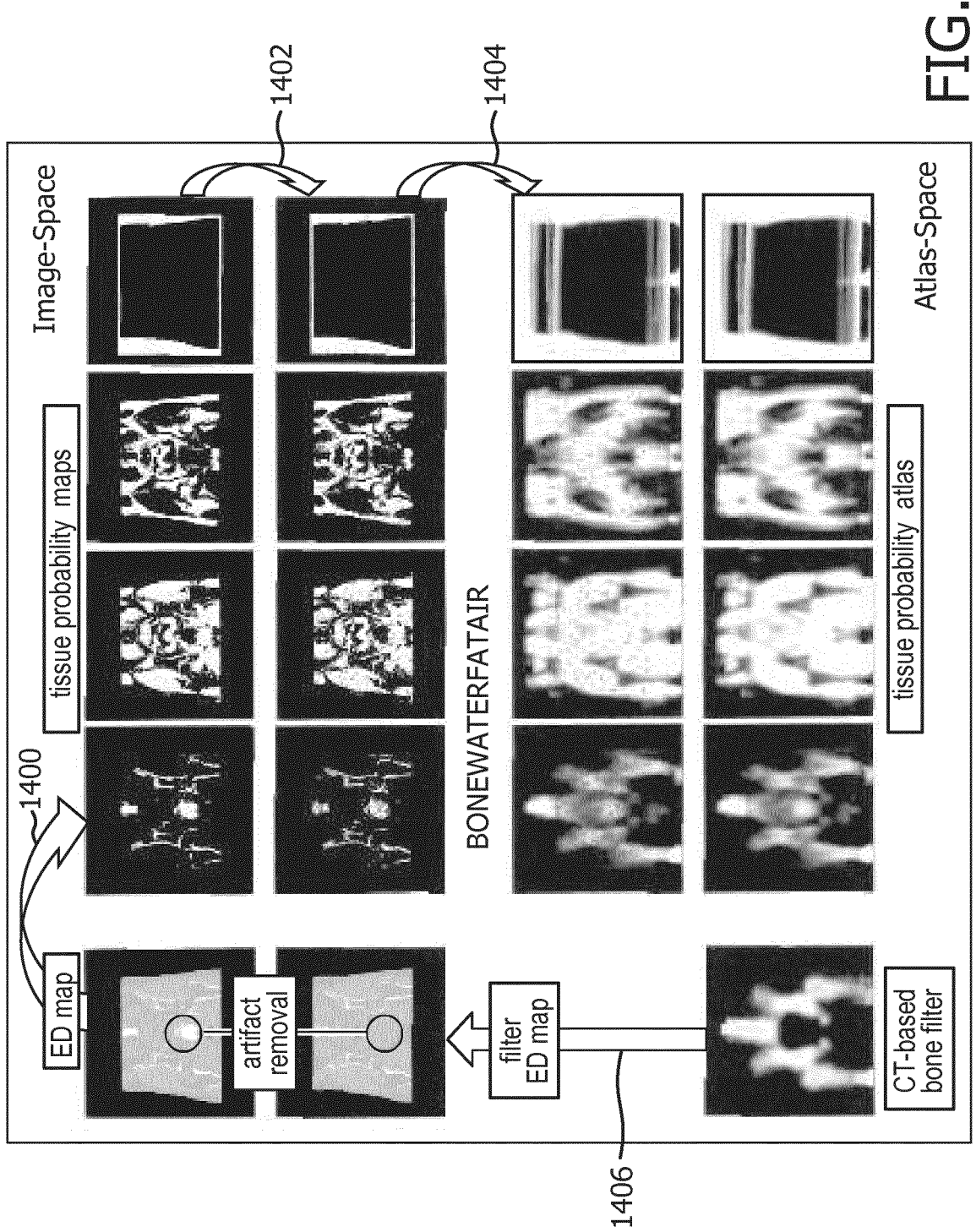
FIG. 14 illustrates a method of registration of an electron density map to a probability atlas.

FIG. 14 illustrates a method of registration of an electron density map to a probability atlas. First in step 1400 tissue maps are generated from electron density maps as derived from a magnetic resonance image. For example they would include artifacts. Next tissue samples are selected in step 1402. These are indicated by dots. Next in step 1404 a similarity transformation is optimized. This may include rotations, isotropic scaling and translation. The similarity transformation is from an image base to an atlas base by evaluating map sample points which are again shown as dots. Finally in step 1406 the CT derived true bone filter map is mapped backwards to image base to extract probable bone and generate a corrected electron density map.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 200 first item
300 medical apparatus
302 magnetic resonance imaging system
304 magnet
306 bore of magnet
308 imaging zone
310 magnetic field gradient coils
312 magnetic field gradient coil power supply
314 radio-frequency coil
316 transceiver
318 subject
320 subject support
326 computer system
328 hardware interface
330 processor
332 user interface
334 computer storage
336 computer memory
340 pulse sequence
340' T1 weighted Dixon pulse sequence
340" ultra short echo time pulse sequence
342 magnetic resonance data
344 magnetic resonance image
344' in-phase image
346 thresholded image
348 bone enhanced image
350 control module
352 image reconstruction module
354 image processing module
356 background removal module
400 medical apparatus
402 fat image
404 water image
406 tissue classification map
408 DDR image
410 anatomical atlas image filter module
500 medical apparatus
502 nuclear medical imaging detector
504 nuclear medical imaging electronics
506 radioisotope
508 gamma ray
510 spatially dependent tissue attenuation map
512 nuclear medical imaging data
514 nuclear medical image
516 tissue attenuation map generation module
600 in-phase image
602 pre-processing of in-phase image
604 thresholding
606 background removal
608 DRR bone image
610 fat image
612 water image
614 tissue classification map
616 DRR tissue classification map
700 MR Image acquisition
702 echo 1
704 echo 2
706 Dixon reconstruction
708 In-phase image
710 water image
712 fat image
714 Tissue classification and electron bulk density assignment
716 bone enhanced image
718 Bone probability atlas
720 ED density map
722 Filtering
724 filtered bone-enhanced image
726 Filtered ED map
1000 medical apparatus
1002 medical image
1004 filtered medical image
1006 anatomical atlas based filter module
1100 medical apparatus
1102 filtered image

The invention claimed is:

1. A medical apparatus comprising:
a magnetic resonance imaging system for acquiring magnetic resonance data from an imaging zone;

a processor configured to control the medical apparatus;
a memory configured to store machine executable instructions wherein execution of the instructions causes the processor to:
  acquire T1 weighted magnetic resonance data from a selected anatomical region of a patient using a pulse sequence that specifies an echo time greater than 400 microseconds (µs);
  reconstruct a magnetic resonance image using the T1 weighted magnetic resonance data;
  generate a thresholded image by thresholding the magnetic resonance image to emphasize bone structures and suppressing tissue structures in the magnetic resonance image;
  generate a bone-enhanced image by applying a background removal algorithm to the thresholded image;
  register a probabilistic atlas to the bone-enhanced image, wherein after registration the atlas indicates a probability of a voxel in the bone-enhanced image as being bone, wherein the probabilistic atlas is a deformable model indicative of locations of bone tissue in the selected anatomical region;
  set the voxel in the bone-enhanced image to a predetermined value indicating no bone tissue if the probability is below a predetermined probability.

2. A medical apparatus comprising:
a magnetic resonance imaging system configured to acquire magnetic resonance data from an imaging zone;
a processor configured to control the medical apparatus;
a memory configured to store machine executable instructions wherein execution of the instructions causes the processor to:
  acquire the magnetic resonance data using a pulse sequence that specifies an echo time greater than 400 microseconds (µs), wherein the pulse sequence is a T1 weighted Dixon pulse sequence,
  reconstruct a magnetic resonance image using the magnetic resonance data, wherein the magnetic resonance image is an in-phase image;
  threshold the magnetic resonance image to emphasize bone structures and suppressing non-bone tissue structures in the magnetic resonance bone image;
  enhance bone in the magnetic resonance image by applying a background removal algorithm to the thresholded magnetic resonance image;
  register a probabilistic atlas to the bone-enhanced image, the probabilistic atlas being a deformable model indicating locations of bone tissue of typical subject anatomy wherein after registration the atlas indicates a probability of each voxel in the bone-enhanced image being bone;
  set each voxel in the bone-enhanced image to a predetermined value indicating no bone tissue if the probability is below a predetermined probability threshold;
  reconstruct a fat image and a water image from the magnetic resonance data; and
  generate a tissue classification map using the fat image, the water image, and the bone-enhanced image.

3. The medical apparatus of claim 2, wherein execution of the instructions further causes the processor to generate a tissue digitally reconstructed radiograph image by projecting the tissue classification map onto a chosen two-dimensional plane.

4. The medical apparatus of claim 2, wherein execution of the instructions further causes the processor to generate an electron density map using the tissue classification map.

5. The medical apparatus of claim 4, wherein the medical apparatus further comprises a radiotherapy simulation system, wherein execution of the instructions further causes the processor to:
  receive therapy parameters; and
  generate a radio-therapy treatment plan using the radiotherapy simulation system with the therapy parameters and the electron density map.

6. The medical apparatus of claim 2, wherein the medical apparatus further comprises a nuclear medical imaging system integrated into the magnetic resonance imaging system, wherein execution of the instructions causes the processor to:
  generate a spatially dependent tissue attenuation map descriptive of the attenuation of gamma radiation by a subject using the tissue classification map;
  acquire nuclear medical imaging data using the nuclear medical imaging system; and
  reconstruct a nuclear medical image using the nuclear medical imaging data and the spatially dependent tissue attenuation map.

7. The medical apparatus of claim 6, wherein the nuclear medical imaging system is a positron emission tomography system or a single-photon emission computed tomography system.

8. The medical apparatus of claim 1, wherein execution of the instructions causes the processor to apply a contrast inversion filter to the magnetic resonance image before generating the thresholded image.

9. The medical apparatus of claim 1, wherein execution of the instructions further causes the processor to generate a bone enhanced digitally reconstructed radiograph by projecting the bone enhanced image onto a selected two-dimensional plane.

10. A method of controlling a processor of a magnetic resonance imaging system for acquiring magnetic resonance data from an imaging zone, the method comprising:
  control the magnetic resonance imaging system to acquire the magnetic resonance data using a pulse sequence which specifies an echo time greater than 400 microseconds (µs), wherein the pulse sequence is a T1 weighted Dixon pulse sequence and wherein the magnetic resonance image is an in-phase image;
  reconstructing an in-phase a magnetic resonance image using the magnetic resonance data;
  reconstructing a fat image and a water image from the magnetic resonance data;
  generating a thresholded image by thresholding the in-phase magnetic resonance image to emphasize bone structures and suppressing non-bone tissue structures in the magnetic resonance image;
  generating a bone-enhanced image by applying a background removal algorithm to the thresholded image;
characterized in that the method further includes:
  registering a probabilistic anatomical atlas to the bone-enhanced image, wherein after registration the atlas indicates a probability of a voxel in the bone-enhanced image as being bone;
  set each voxel in the bone-enhanced image to a predetermined value indicating no bone tissue if the probability is below a predetermined probability threshold; and
  combining the fat image, the water image, and the bone-enhanced image to generate a tissue classification map.

11. A non-transitory computer-readable medium carrying software which controls the processor to perform the method of claim 10.

* * * * *